(12) United States Patent
Kligerman et al.

(10) Patent No.: US 6,447,754 B1
(45) Date of Patent: Sep. 10, 2002

(54) ORAL RINSE METHODS AND COMPOSITIONS

(75) Inventors: Alan E. Kligerman, Egg Harbor Township; Sarah Rogers, Mays Landing, both of NJ (US)

(73) Assignee: AkPharma Inc., Pleasantville, NJ (US)

( * ) Notice: Subject to any disclaimer, the term of this patent is extended or adjusted under 35 U.S.C. 154(b) by 0 days.

(21) Appl. No.: 09/490,266

(22) Filed: Jan. 24, 2000

(51) Int. Cl.⁷ .......................... A61K 7/16; A61K 33/06; A23L 2/52; B65D 17/00
(52) U.S. Cl. .......................... 424/49; 424/57; 424/682; 426/74; 426/590; 426/648; 426/650; 426/597; 426/599; 206/633
(58) Field of Search ..................... 424/49–58; 206/620; 426/86, 590

(56) References Cited

U.S. PATENT DOCUMENTS

| | | | |
|---|---|---|---|
| 1,592,395 A | * | 7/1926 | Sulzberger |
| 1,770,118 A | * | 7/1930 | Williams |
| 1,889,111 A | * | 11/1932 | Serr |
| 2,062,897 A | * | 12/1936 | Michel et al. ................ 206/47 |
| 3,202,275 A | * | 8/1965 | Loughary .................... 206/65 |
| 3,252,803 A | * | 5/1966 | Belasco ........................ 99/78 |
| 3,952,092 A | | 4/1976 | Bowen et al. |
| 4,206,209 A | | 6/1980 | Kracauer |
| 4,261,253 A | * | 4/1981 | Smith, I ..................... 493/189 |
| 4,312,889 A | * | 1/1982 | Melsheimer ................. 426/86 |
| 4,378,069 A | * | 3/1983 | Franco ........................ 206/620 |
| 4,498,591 A | * | 2/1985 | Smith, II .................... 206/620 |
| 4,826,675 A | | 5/1989 | Gaffar et al. |
| 4,871,091 A | * | 10/1989 | Preziosi ....................... 222/92 |
| 4,935,227 A | | 6/1990 | Duckworth |
| 4,980,153 A | | 12/1990 | Jackson et al. |
| 5,002,189 A | * | 3/1991 | Sahi ........................... 206/633 |
| 5,015,464 A | | 5/1991 | Straw |

(List continued on next page.)

FOREIGN PATENT DOCUMENTS

| | | |
|---|---|---|
| WO | WO 96/19228 | 6/1996 |
| WO | 97 30601 | * 8/1997 |
| WO | 99 08550 | * 2/1999 |

OTHER PUBLICATIONS

A. H. Brook et al., "Calcium Glycerophosphate and Dental Plaque," *Caries Res.*, 9:156–162 (1975).

W.H. Bowen, "The Cariostatic Effect of Calcium Glycedrophosphate in Monkeys," *Caries Res.*, 6:43–51 (1972).

(List continued on next page.)

*Primary Examiner*—Shep K. Rose
(74) *Attorney, Agent, or Firm*—Akin, Gump, Strauss, Hauer, & Feld, L.L.P.

(57) ABSTRACT

Methods of freshening and reducing acidity in both the mouth and the throat of a mammal, such as a human, include taking into the mouth an aqueous solution of calcium glycerophosphate (CGP) in an amount effective to reduce the acidity, maintaining the solution in the mouth, and swallowing the aqueous solution in order to freshen and reduce acidity in both the mouth and the throat. The methods are convenient for use at any place and any time and do not have the inconveniences and limitations of conventional oral rinse or oral hygiene methods, such as the need for proximity to private or public plumbing facilities. Swallowable oral rinse compositions include an aqueous solution of CGP in an amount effective to freshen and reduce acidity in both the mouth and the throat of a mammal, such as a human, and at least one of a sweetening agent and a flavoring agent. The oral rinse compositions comprising CGP are preferably safe for ingestion even by children. Conveniently portable systems for delivery of a single serving of an oral rinse composition may be in the form of a single unit or a multi-unit package, suitable for delivery of a single serving of oral rinse compositions for use at any time and any place with great convenience.

22 Claims, 4 Drawing Sheets

U.S. PATENT DOCUMENTS

| | | | |
|---|---|---|---|
| 5,026,539 A | | 6/1991 | Jackson et al. |
| 5,087,444 A | | 2/1992 | Jackson et al. |
| 5,112,600 A | | 5/1992 | Jackson et al. |
| 5,174,658 A | * | 12/1992 | Cook et al. .................... 383/33 |
| 5,227,154 A | | 7/1993 | Reynolds |
| 5,310,542 A | | 5/1994 | Au et al. |
| 5,350,240 A | * | 9/1994 | Billman et al. ............. 383/104 |
| 5,362,480 A | | 11/1994 | Peekskill et al. |
| 5,378,131 A | | 1/1995 | Greenberg |
| 5,409,902 A | | 4/1995 | Carson et al. |
| 5,416,075 A | | 5/1995 | Carson et al. |
| 5,449,509 A | | 9/1995 | Jackson et al. |
| 5,490,978 A | | 2/1996 | Spaltro et al. |
| 5,571,502 A | | 11/1996 | Winston et al. |
| 5,603,922 A | | 2/1997 | Winston et al. |
| 5,605,675 A | | 2/1997 | Usen et al. |
| 5,614,175 A | | 3/1997 | Winston et al. |
| 5,665,415 A | * | 9/1997 | Kligerman, I et al. ...... 426/590 |
| 5,672,351 A | | 9/1997 | Chikindas et al. |
| 5,747,004 A | | 5/1998 | Giani et al. |
| 5,801,226 A | | 9/1998 | Cummins et al. |
| 5,817,296 A | * | 10/1998 | Winston, III et al. ......... 424/49 |
| 5,827,505 A | | 10/1998 | Hughes et al. |
| 5,833,954 A | | 11/1998 | Chow et al. |
| 5,833,957 A | * | 11/1998 | Winston, II et al. .......... 424/49 |
| 5,840,322 A | | 11/1998 | Weiss et al. |
| 5,866,102 A | * | 2/1999 | Winston, I et al. ........... 424/52 |
| 5,869,119 A | * | 2/1999 | Kligerman, II et al. ....... 426/74 |
| 6,319,490 B1 | * | 11/2001 | Parker, III ................... 424/55 |

OTHER PUBLICATIONS

S. J. Wycoff et al., "The Effect of Mouthrinse Containing Calcium Glycerophosphate on the Chemical Composition and Development of Plaque in Humans," *J. Dent. Res.*, 59(1):23–28 (Jan. 1980).

D. O. Born, "Super Solutions for Tooth Decay," *The Saturday Evening Post*, pp. 16, 17 (Jan./Feb. 1987).

H. Nordbö et al., "Desorption of Salivary Proteins from Hydroxyapatite by Phytic Acid Glycerophosphate and the Plaque–Inhibiting Effect of the Two Compounds in Vivo," J. Dent. Res. , 51(3):800, 801 (May—Jun. 1972).

O–T–Cs—Oral Care, "Mouthwash arena in need of a boost," *Chain Drug Review*, p. 34 (Jan. 4, 1999).

M.W. Dodds et al., "The relationship between plaque pH, plaque acid anion profiles, and oral carbohydrate retention after ingestion of several 'reference foods' by human subjects," *J. Dent Res*, 67(5):861–5 (May 1988)—Abstract Only.

S. Kalfas et al., Effect of pH on acid production from sorbitol in washed cell suspensions of oral bacteria, *Caries Res*, 24(2):107–12 (1990)—Abstract Only.

M.W. Dodds et al., "Effects of dietary sucrose levels on pH fall and acid–anion profile in human dental plaque after a starch mouth–rinse," *Arch Oral Biol*, 31(8):509–12 (1986)—Abstract Only.

P.L. Schroeder et al., "Dental erosion and acid reflux disease," *Ann Intern Med*, 122(11):809–15 (Jun. 1, 1995).

P. Lingstrom et al., "Effect of frequent consumption of starchy food items on enamel and dentin demineralization and on plaque pH in situ," *J Dent Res*, 73(3):652–60 (Mar. 1994)—Abstract Only.

L.M. Macpherson et al., "An in vitro stimulation of the effects of chewing sugar–free and sugar–containing chewing gums on pH changes in dental plaque," *J Dent Res*, 72(10):1391–7 (Oct. 1993)—Abstract Only.

B.G. Bibby et al., "Oral food clearance and the pH of plaque and saliva," *J Am Dent Assoc*, 112(3):333–7 (Mar. 1986)—Abstract Only.

D.C. Abelson et al., "The effect of saliva on plaque pH in vivo," *J Dent Res*, 60(9):1634–8 (Sep. 1981)—Abstract Only.

A. Millward et al., "Continuous monitoring of salivary flow rate and pH at the surface of the dentition following consumption of acidic beverages," *Caries Res*, 31(1):44–9 (1997)—Abstract Only.

G.L. Hays et al., "Salivary pH while dissolving vitamin C–containing tablets," *Am J Dent*, 5(5):269–71 (Oct. 1992)—Abstract Only.

K. Nilner et al., "Effect of a buffering sugar–free lozenge on intraoral pH and electrochemical action," *Acta Odontol Scand*, 49(5):267–72 (Oct. 1991)—Abstract Only.

F.M. Eggert et al., "The pH of gingival crevices and periodontal pockets in children, teenagers and adults," *Arch Oral Biol*, 36(3):233–8 (1991)—Abstract Only.

G. Maglis et al., "Determination of saliva pH in periodontal disease patients and a control group," *Rev Dent Chile*, 80(2):70–2 (Aug. 1989)—Abstract Only.

C.M. Christensen et al., "Salivary changes in solution pH: a source of individual differences in sour taste perception," *Physiol Behav*, 40(2):221–7 (1987)—Abstract Only.

I.D. Mandel, "The role of saliva in maintaining oral homeostasis," *Journal of the American Dental Association*, 8(8:298 (7) (1989)—Abstract Only.

Lyda Associates Inc.® 1990, "Dental erosion by fruit," *Nutrition Research Newsletter*, 9(1):6(2) (Jan. 1990)—Abstract Only.

T. Walsh, "Do–it–yourself rinses. (Your Healthy Smile)," *Prevention*, 47(6):42(2) (Jun. 1995)—Abstract Only.

J.R. Newland, "Oral ulcers: keys to differential and definitive diagnosis," *Consultant*, 29(5):157(11) (May 1989).

P.J. Moynihan et al., "A comparison of the relative acidogenic potential of infant milk and soya infant formula: a plaque pH study," *Int J Paediatr Dent*, 6(3):177–81 (Sep. 1996)—Abstract Only.

M.E. Thomson et al., "In vivo and intra–oral investigations into the cariogenic potential of human milk," *Caries Res*, 30(6):434–8 (1996)—Abstract Only.

Nutrition Research Newletter of John Wiley & Sons, Inc., "Breast Milk and Dental Caries," *Nutrition* Research, XVI(4):37, 48 (Apr. 1997).

M.M. Von Burg et al., "Baby bottle tooth decay: a concern for all mothers," *Pediatr Nurs*, 21(6):515–9, quiz 520–1 (Nov.–Dec. 1995)—Abstract Only.

R.D. Holt et al., "The weaning diet and dental health," *Br Dent J*, 181(7):254–9 (Oct. 5, 1996)—Abstract Only.

Jamie Talan, Newsday Newspaper Article entitled "Scientists getting nearer to knocking out cavities without using fluoride," p. D4 (Jan. 1997).

Lyda Associates Inc.® 1990, "Dental properties of soft drinks," *Nutrition Research Newsletter*, 9(1:7(1) (Jan. 1990).

C.C. Schurer–Maly et al., "Smoking and pH response to H2–receptor antagonists," *Scand J Gastroenterol*, 24(10):1172–8 (Dec. 1989)—Abstract Only.

L.A. Elson et al., "The Sugar Content And The pH Of The Smoke Of Cigarette, Cigar And Pipe Tobaccos In Relation To Lung Cancer," *Int J Cancer*, 9(3):666–675 (1972)—Abstract Only.

Single Sheet from *Environmental Nutrition*, with the caption "Say Cheese," p. 21 (Oct. 1996).

D. Birkhed et al., "pH Changes in Human Dental Plaque from Lactose and Milk before and After Adaptation," *Caries Res* 27:43–50 (1993)—Abstract Only.

C.J. Thomas et al., "Astringent subqualities in acids," *Chem Senses*, 20(6):593–600 (Dec. 1995)—Abstract Only.

E. Bashir et al., Department of Cariology, School of Dentistry, Karolinska Institutet, Huddinge, Sweden, "Site specificity of citric acid retention after an oral rinse," *Caries Res*, 29(6):467–9 (1995)—Abstract Only.

The American Dietetic Association®, Single Information Sheet, "Fig. 1. Definitions of oral health terms," (Mar. 19, 1997).

News Bites, Single Sheet, "Sports Drinks: Bad for Teeth?" *HealthNews*, p. 8 (Apr. 15, 1997).

Single page, "Medical Update—Heartburn and Tooth Trouble," *Consumer Reports on Health*, p. 106 (Sep. 1995).

T.H. Grenby, "Comparison of the Cariostatic Effects of Calcium and Sodium Glycerophosphates in Rats,"*Helv. Odont. Acta*, 17:54, 55 (Oct. 1973).

A.H. Brook et al., "A Clinical Study of the Effect of Calcium Glycerophosphate," *Helv. Odont. Acta*, 17:55 (Oct. 1973).

Single Sheet, last paragraph, *Food Processing*, p. 659.

*Akademiia Nauk SSSR*, Dobladay, 161(1):244–247 (1965).

P. Vahl et al., "Examination of the pH of saliva in children and juveniles in relation to caries, gingivitis and oral hygiene," *Stomatol DDR*, 39(4):253–8 (Apr. 1989).

\* cited by examiner

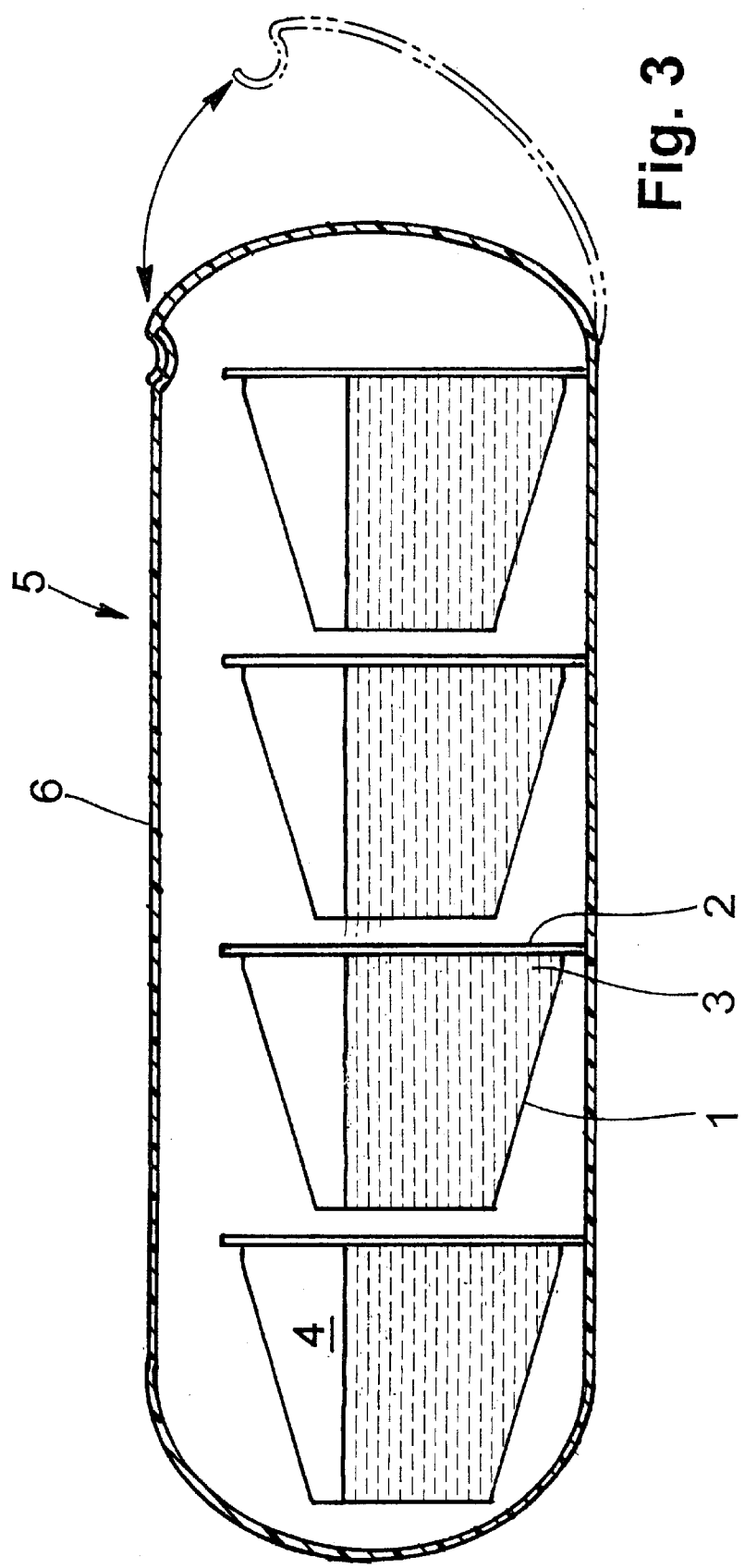

ORAL RINSE METHODS AND COMPOSITIONS

BACKGROUND OF THE INVENTION

The invention relates to methods and compositions useful in promoting oral hygiene.

Most people are aware of the need to take measures frequently to promote oral hygiene, especially between meals or immediately after a meal during the day. Many enjoy the feeling of a freshened mouth after such measures and would be willing to take oral hygiene measures directly after each meal or during intermediate periods between meals, but find such measures to be either inconvenient or awkward. For example, although many consumers may desire to freshen their mouth or throat or to reduce the acidity in their mouth or throat during the day, there are several factors which prevent them from doing so.

One factor is that such measures may be inconvenient, for a variety of reasons. It may be that they are traveling in a vehicle or away from home for extended periods of time during the day in which they do not have easy access to a sink, a bathroom or other plumbing facilities required to use a conventional oral hygiene product, such as a conventional mouthwash.

Another factor may be that they are uncomfortable performing oral hygiene measures away from home at places such as at the workplace or at school, because they are unwilling to be seen in the shared restrooms at work or at school using and spitting out a mouthwash, or because they find offensive the idea of spitting something out from their mouth into a sink used by many others in a public restroom. Also, they may be uncomfortable being seen at work or school carrying around the items needed to take such measures, such as a cup and a bottle of mouthwash, or a toothbrush and toothpaste.

While the prior art has given much attention to the development of a variety of oral hygiene compositions, such as mouthwashes, mouthrinses and toothpastes, in a variety of different flavors and containing active ingredients effective at addressing various aspects of oral hygiene, little attention has heretofore been given to the development of oral hygiene compositions or methods which can be used anywhere and at any time without the need for proximity to a sink or plumbing facilities. Thus, nearly all of the prior art mouthrinses and mouthwashes are either alcohol-based or contain ingredients not intended for other than marginal or incidental ingestion. These products also present the burden upon consumers of protecting themselves and their children from accidental ingestion in either minor or major quantities and are often of limited usefulness in oral hygiene care because they are not indicated for use by children. Indeed, most conventional mouthwashes contain poison control warning labels or other such warning labels with regard to accidental ingestion by children. Moreover, these products tend to "sting" the delicate oral and throat tissues.

Manufacturers of conventional mouthwashes and mouthrinses have either not known how to make a product without these drawbacks or they have been unwilling to carry out the research and development necessary to develop a new approach to mouthwashes and mouthrinses beyond what has been the norm for the last seventy years. Thus, little attention has heretofore been given to the development of a mouthwash or mouthrinse that is suitable for ingestion, even by children, much less a mouthrinse that provides upon ingestion an additional nutritional or hygienic benefit, such as providing a source of calcium or freshening the throat.

Moreover, the prior art has given little attention to the convenience of use of oral hygiene compositions and methods. For example, little attention has heretofore been given to developing methods or compositions for the use of oral rinse compositions in a conveniently portable fashion, to make it more practical to use such compositions at any place or at any time.

Furthermore, the prior art compositions and methods do not provide the convenience of a bifunctional product or method, such as one which can be used for the oral hygiene of both the mouth and the throat. For example, little attention has been given to providing the consumer with a single multi-functional product or method for use in oral hygiene that can be used or performed at any time or any place for freshening and reducing acidity of both the mouth and the throat. Also, the conventional oral rinse compositions present the detriments and risks attendant to damaging the naturally occurring flora of micro-organisms present in the oral cavity.

Thus, there exists a great but unmet need for oral hygiene methods and compositions having the features of swallowability, safety for ingestion by children, convenience of portability, convenience of use anywhere and at any time, and multi-functionality. Compositions and methods with these features would promote oral hygiene by facilitating more frequent and widespread use of oral hygiene methods and compositions by many consumers, including children. The present invention is directed to these needs.

BRIEF SUMMARY OF THE INVENTION

The present invention provides a method of freshening and reducing acidity in both the mouth and the throat of a mammal. The method comprises taking into the mouth an aqueous solution comprising calcium glycerophosphate (CGP) in an amount effective to reduce the acidity in the mouth and the throat of the mammal; maintaining the aqueous solution in the mouth for. a period of time sufficient to freshen and reduce the acidity in the mouth of the mammal, and thereafter swallowing the aqueous solution, whereby both the mouth and the throat of the mammal are freshened, and the acidity in both the mouth and the throat of the mammal is reduced. The amount of CGP present in the aqueous solution may be, for example, from about 0.1% to about 4% by weight. The period of time may be, for example, from about 2 to about 30 seconds. Preferably, the ingredients of the solution other than CGP and water are selected so as to make the solution ingestible even by children.

In one aspect of the method of the invention, the oral acidity may result from ingestion by the mammal of an acidic ingestible or from a condition such as post-nasal drip, gastroesophageal reflux, acidophilic bacterial metabolism, bacterial fermentation of food particles and dental plaque. Acidic ingestibles include acidic beverages such as coffee, beer, lemonade, soft drinks, fruit juice, tomato juice, wine and at least partially dehydrated versions thereof. Acidic ingestibles also include acidic foods such as pickles, citrus-flavored water ices and sherbets, salsa, pickled herring, sweet and sour soup, sauerkraut and foods containing tomato sauce. Acidic ingestibles also include acidic medicaments such as aspirin, other non-steroidal anti-inflammatory drugs (NSAIDS), and vitamin C (ascorbic acid).

In another aspect, the method of the invention includes selectively dissolving certain carboxylic acid-containing particles in the mouth of a mammal by maintaining the composition of the invention in the mouth of the mammal for a period of time sufficient to selectively dissolve the acidic particle.

The invention also includes a swallowable oral rinse composition for freshening and reducing acidity in both the mouth and the throat of a mammal. The composition comprises an aqueous solution of CGP in an amount effective to freshen and reduce acidity in both the mouth and the throat of the mammal, and at least one of a sweetening agent in an amount effective to render the composition palatable and a flavoring agent in an amount effective to impart a pleasant flavor to the composition.

In one aspect, the flavoring agent is provided to the composition in the form of a concentrate comprising a flavoring composition and a coloring agent. In a preferred aspect, the water is purified by method s such as reverse-osmosis, filtration and distillation.

The invention also includes a conveniently portable system for delivery of a single serving of an oral rinse composition. The portable system comprises a non-resealable container having a capacity sufficient to contain a single-serving of the oral rinse composition. The container can be opened by an adult or a child without the use of any tools and can be conveniently carried on the person in a pocket.

In another aspect of the invention, the portable system is itself a unit of a portable, multi-unit package or container containing an oral rinse composition.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention there are shown in the drawings embodiments which are presently preferred. It should be understood, however, that the invention is not limited to the precise arrangements and instrumentalities shown. In the drawings:

FIG. 1, comprising

FIG. 2, comprising

FIG. 3 is a schematic side view of a conveniently portable system of the invention in the form of a "clamshell-type" reusable plastic multi-unit container for delivery of multiple single servings of an oral rinse composition.

DETAILED DESCRIPTION OF THE INVENTION

Figure 1B:
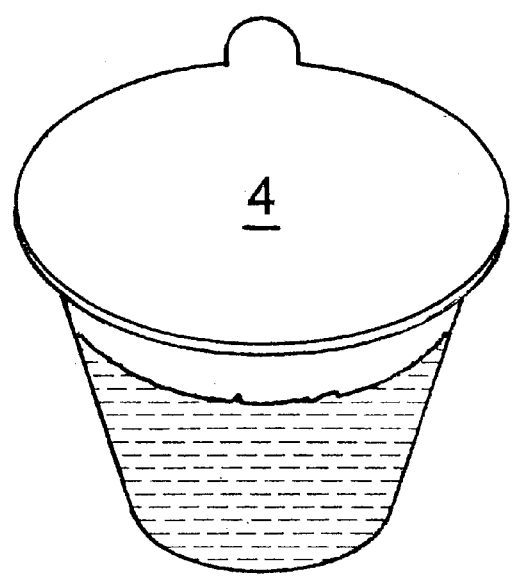
FIGS. 1a and 1b, is a schematic side view and a schematic perspective view from above, respectively, of a conveniently portable system of the invention in the form of a single unit for delivery of a single serving of an oral rinse composition.
Figure 1A:
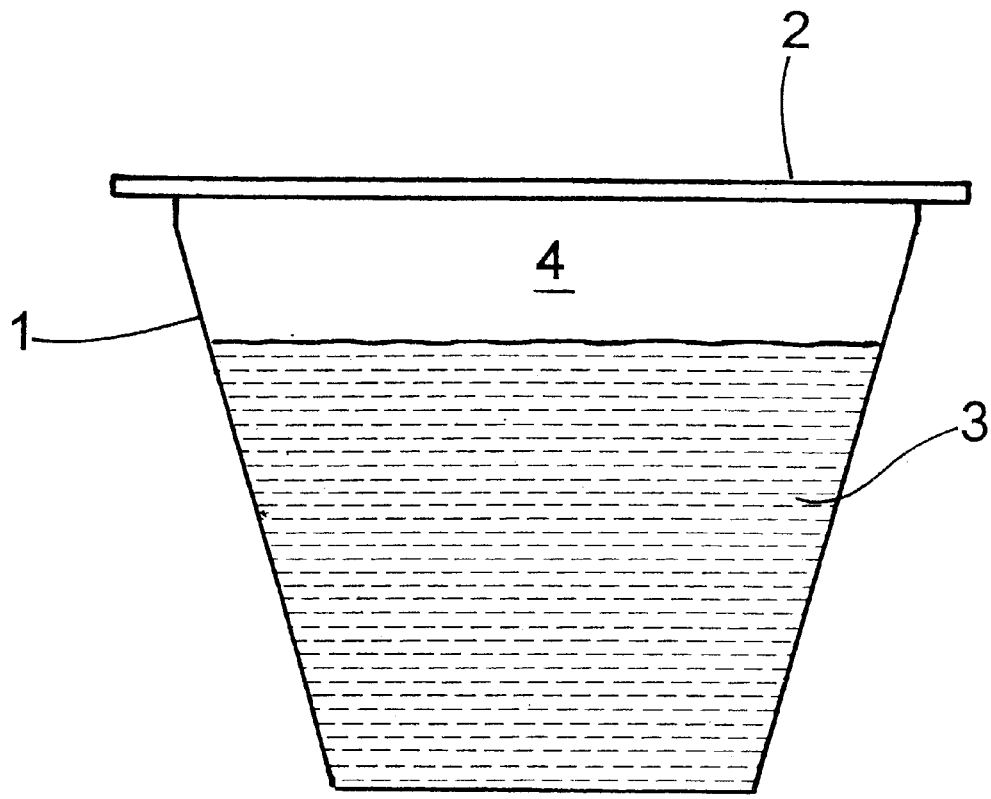

The methods and compositions of the present invention relate to swallowable oral rinse compositions employing CGP, and thus have the advantageous feature of providing methods and compositions which can be performed or used at any place and at any time for oral hygiene, including freshening and reducing acidity of both the mouth and the throat. Unlike conventional oral rinse methods and compositions, the methods and compositions of the present invention do not require proximity to a sink or plumbing facilities for use, and can thus be performed or used at any place or any time. The compositions of the present invention are intended to be swished in the mouth and then swallowed, in contrast to conventional oral rinse compositions, which are intended to be swished and then spit-out, and not swallowed. With this feature, the methods and compositions of the present invention eliminate the awkwardness and barriers associated with having to use conventional oral rinse methods or compositions in non-private places such as public restrooms during the day, for example at work or school. The present invention also eliminates the inconvenience of carrying around accessories such as cups and bottles required to use conventional oral rinse methods and compositions.

Furthermore, the methods and compositions of the present invention are multi-functional in that they improve the oral hygiene of both the mouth and the throat. The methods and compositions of the present invention control oral microorganisms by gently modifying the oral environment to render it inhospitable to acidophilic and acidproducing microorganisms, rather than by using a "shotgun" bactericidal approach, as in conventional methods and compositions, which can damage host tissue. Moreover, conventional oral rinse methods and compositions are not intended to be swallowed for treatment of other areas of the upper gastro-intestinal tract, such as the throat. Also, since the methods and compositions of the present invention employ swallowable oral rinse compositions, they have the advantageous feature of being safe for ingestion by children, and even being nutritious in that they provide a source of calcium and phosphorus and/or phosphate, unlike conventional oral rinse methods.

One aspect of the invention includes oral rinse methods and compositions employing calcium glycerophosphate (CGP). Calcium glycerophosphate is also known as 1,2,3-propanetriol, mono(dihydrogen phosphate) calcium salt (1:1), calcium glycerinophosphate, calcium phosphoglycerate and Neurosin®. It has a molecular formula of $C_3H_7CaO_6P$ and a formula weight of 210.14 (anhydrous). It may exist as a hydrate, including the monohydrate and the dihydrate. Three CGP isomers exist, namely β-glycerophosphoric acid, calcium acid and calcium salt ($HOCH_2CH(OH)CH_2OPO_3Ca$). Any one isomer, or any combination of two or more isomers may be used as the CGP according to the invention. A commercially available form of CGP is a mixture of calcium β- and DL-α-glycerophosphates, and this is a preferred CGP according to the invention. The preferred form of CGP is food grade CGP according to Foods Chemical Codex (FCC) III, and may be obtained from Gallard Schlesinger Company, Carl Place, N.Y. 11514, which is a distributor for Dr. Paul Lohmann GmbH KG of Emmerthal, Germany; Seppic (France); or Astha (India), among others.

CGP is odorless, almost tasteless, and forms a fine, slightly hygroscopic powder. CGP may also be formed into tablets, and may be dissolved into water. The solubility of CGP is about 1 gram in about 50 mL of water. FCC III lists CGP as a nutrient/dietary supplement, but does not indicate that CGP is either an alkali or a buffer/neutralizing agent. Thus, CGP is known in the art to be useful as a dietary supplement for calcium and phosphorus and/or phosphate, where CGP contains 19 wt % calcium.

The CGP may be used alone or in combination with other calcium salts, such as calcium carbonate, calcium acetate, calcium oxide, calcium hydroxide, calcium phosphate, calcium lactate and calcium citrate. As CGP is relatively expensive, combining CGP with one or more calcium salts such as listed above affords a less expensive composition that may be used in the present invention. However, the combination of CGP and one or more additional calcium salts may have solubility properties that are very different from that of CGP alone. One of the surprising advantages of using CGP compared to other calcium salts is that CGP readily dissolves, and stays dissolved, in aqueous solution, which are properties not shown by other calcium salts and compounds The methods of the invention include methods of freshening and reducing acidity in both the mouth and the throat of a mammal. The term "freshening" or "to freshen" as used herein in relation to the mouth of a mammal will be generally understood to mean cleaning, imparting a pleasant feeling or taste to, imparting a clean or a soothing feeling to, and/or removing decaying food particles from the mouth. As used herein in relation to the throat, the term will be understood to mean cleaning or imparting a pleasant, clean, and/or soothing feeling to the throat.

The term "reducing acidity" or "to reduce the acidity of" as used herein in relation to the mouth or the throat of a mammal means to raise and/or maintain the pH of a surface or a portion of the mouth or the throat or the saliva therein to or at a pH of about 6.0 or higher for up to about five hours after ingestion of a cariogenic (i.e., leading to the development of dental cavities) substance. The surface or portion of the mouth or the throat or the saliva therein may include, by way of example and not by way of limitation, the surface or a portion of the teeth, the gums, and the back of the throat of a mammal.

The mammal is usually a human, but can also be a domestic animal such as a dog or a cat. When the mammal is a human, a human of any age, except an infant, is included.

In the methods of the invention, an aqueous solution comprising calcium glycerophosphate (CGP) is taken into the mouth of a mammal in an amount effective at reducing acidity in the mouth and throat of the mammal. The aqueous solution of CGP may be taken into the mouth by any known route of administering an oral rinse composition, such as by sipping or pouring from a cup or from a small package, packet or container, or by sipping or intaking through a straw or by taking from a medicine dropper or a waterbowl in the case of a domestic animal, or by spraying from a suitable atomizer or the like.

In one embodiment, a volume of about 5–10 milliliters is taken into the mouth of a human. In a preferred embodiment, a volume of about 8 milliliters is taken into the mouth of a human. The amount of CGP present in the aqueous solution is any amount effective at freshening and reducing acidity in both the mouth and the throat of the mammal. For example, in one embodiment, the amount of CGP present in the aqueous solution ranges from about 0.1% to about 4% by weight. In a preferred embodiment, the amount of CGP is present in the aqueous solution in an amount from about 1% to about 1.15% by weight.

The method also comprises maintaining the aqueous solution in the mouth for a period of time sufficient to freshen and reduce acidity in the mouth of the mammal. The solution is maintained in the mouth in the same manner as any other oral rinse composition or mouthwash, such as by gargling or by maintaining the solution in a closed mouth, using the cheek, tongue and/or facial muscles to effect swishing or swirling of the solution around in a closed mouth in order to maximize the cleaning effect and the amount of contact with oral surfaces. Alternatively, the solution may simply be maintained in a closed or partially open mouth for a period of time sufficient to freshen and reduce acidity in the mouth. Also, the solution could be brushed around the teeth, tongue and gums, for example with a toothbrush, but this method partially defeats the convenience of not having to carry around oral paraphernalia.

The period of time for which the solution is maintained in the mouth is any period of time sufficient to freshen and reduce acidity in the mouth. This will, of course, vary with the type of mammal and the degree of freshening and reduction of acidity desired. For example, in a human, the period of time ranges in one aspect from about 2 seconds to about 30 seconds. Preferably, the period of time is from about 5 seconds to about 10 seconds.

The method also comprises swallowing the aqueous solution after maintaining the solution in the mouth as described above. A result of swallowing the aqueous solution is that the throat of the mammal, as well as the mouth, is freshened and the acidity in the throat of the mammal is reduced as well.

In a preferred aspect, the ingredients of the aqueous solution other than CGP and water are selected so as to make the solution ingestible even by children. For example, the aqueous solution should be free of alcohol or other active ingredients which warrant poison control labeling or hazard labeling indicating that the composition is to be kept away from children. Such compositions are described herein in the Examples. Not only is ingestion of these compositions by children safe, it is also nutritious, since CGP is a source of calcium and phosphorus and/or phosphate listed in the FCC III as a nutrient/dietary supplement.

There are many factors or conditions which may lead to acidity in the mouth and the throat of a mammal such as a human. One of these factors is the residual acidic matter in the mouth or the throat after taking in an acidic ingestible. As used herein, the term "acidic ingestible" means a substance ingested by a mammal and having an acidic property. The term includes, for example, acidic foods, acidic beverages and acidic medicaments.

Examples of acidic beverages, which are included within the term "acidic ingestibles" as used herein and which are commonly acidic, include beer, coffee including decaffeinated coffee, soft drinks including cola, fruit juice, tomato juice, lemonade and wine, and at least partially dehydrated versions thereof.

Examples of acidic foods, which are included within the term "acidic ingestibles" as used herein, include tomato sauce and foods containing tomato sauce, such as spaghetti and pizza, pickles, citrus-flavored water ices and sherbets, salsa, pickled foods, sweet and sour soup, sauerkraut, and the like.

As used herein, acidic ingestibles also include acidic medicaments. Such acidic medicaments include acid-based medicines or oral medications or dietary supplements having acidic active ingredients, excipients, vehicles or formulation ingredients. Such medicaments include, for example, analgesics or anti-inflammatories and vitamins, such as aspirin, ibuprofen and vitamin C (ascorbic acid).

In one aspect, the method of the invention further comprises selectively dissolving an acidic medicament, for example in the form of an acidic particle, in the mouth of a mammal. As used herein, the term "selectively dissolving"

means enhancing the solubility of the acidic medicament in the mouth of a mammal. The acidic particle becomes more soluble and thus more easily dislodged from the teeth or gums by maintaining the solution in the mouth for a period of time sufficient to enhance the solubility of the medicament (See, for example Morrison et al., 1979, *Organic Chemistry*, 3rd Edition, p, 583, Allyn and Bacon, Inc., Boston). The period of time required will vary with the particular acidic medicament. For example, a tablet of aspirin may be taken into the mouth by a human, and immediately after placing the tablet in the mouth, an inventive solution comprising CGP is taken into the mouth and maintained in the mouth for a period of time sufficient to selectively dissolve the aspirin particle.

Alternatively, after taking into the mouth aspirin or a similar acidic medicament, an oral rinse composition of the invention can be used in a method of the invention to remove any residue of the acidic medicament in the mouth and to assist in dissolution of the acidic medicament in the stomach. Thereafter, the solution is swallowed along with the aspirin tablet, now fully dissolved because of the effect of CGP. An advantage of this method is that it reduces the acidity in the gastrointestinal tract from the mouth down to and including the stomach resulting from the acidic particle by virtue of the buffering capacity of CGP. This feature allows the consumer who is highly sensitive to stomach and throat acidity from acidic ingestibles to consume acidic particles, such as aspirin and other acidic medicaments, without the attendant distress which would otherwise result.

Another factor contributing to the acidity in the mouth and the throat of a mammal is bacterial fermentation of food particles remaining on, around or between the teeth after a meal. Yet another factor is the presence of dental plaque upon the teeth or between the teeth and gums. Dental plaque itself is known to be acidic, and dental plaque acids are known to be cariogenic. In addition, bacterial fermentation of food particles on the teeth and dental plaque on the teeth promote a favorable growth environment for acidophilic bacteria in the mouth, and the metabolism of these bacteria presents still another factor which contributes to the acidity of the mouth.

The acidity of the mouth and/or the throat of a mammal may also result from a condition or an illness. For example, during a cold or a sinus infection in a human, the condition of post-nasal drip results in acidity at the back of the throat of the human. This condition also leads to an odor in the throat and mouth due to the contents of the post-nasal drip. Also, the condition of gastroesophageal reflux, particularly from gastroesophageal reflux disease (GERD), a symptom of which is the frequent reflux of stomach acids up through the esophagus, also leads to acidity in the back of the throat of a human, and even into the mouth, where the acidity is known to erode the teeth at the rear of the mouth.

In one aspect of the methods of the invention, the acidity resulting from any one or more of the above factors or conditions in the mouth and/or the throat of a mammal is treated using the multi-functional methods of the invention, which serve the multiple functions of freshening and reducing acidity in both the mouth and the throat. The purposes of reducing acidity in and freshening the throat include to deodorize, freshen and reduce the discomfort and/or distress associated with the acidity resulting from the factors and conditions discussed above, such as GERD, post-nasal drip, and other illnesses or conditions. Advantages of reducing acidity in the mouth, in addition to freshening and cleaning the mouth, may also include retarding the progress of dental caries in the mouth, and/or reducing the acidity of cariogenic dental plaque in the mouth.

The invention also includes swallowable aqueous oral rinse compositions for freshening and reducing acidity in both the mouth and the throat of a mammal (e.g., a human). These swallowable oral rinse compositions may be, for example, in the form of an aqueous mouthrinse or mouthwash. The inventive compositions are useful for freshening and reducing acidity in both the mouth and the throat of a mammal resulting from the various conditions and factors discussed above. As discussed above, the mammal may be any mammal, but is preferably a human or a domestic animal, such as a dog or a cat.

The inventive compositions comprise CGP in an amount effective to freshen and reduce acidity in both the mouth and the throat of the mammal as discussed above. In one aspect, the CGP is present in the aqueous oral rinse composition in an amount from about 0.1% to about 4% by weight. In another aspect, the CGP is present in the aqueous oral rinse composition in an amount from about 1% to about 3% by weight. In a preferred aspect, the CGP is present in an amount from about 1% to about 1.15% by weight. As used herein, unless otherwise indicated, all percentages are percent by weight of the total composition.

The inventive compositions further comprise a sweetening agent or a flavoring agent, or comprise both a sweetening agent and a flavoring agent. When present, the sweetening agent is preferably effective at reducing or removing bitterness from the composition, and is present in an amount effective to render the composition palatable and preferably pleasant in taste. A number of suitable sweetening agents are known to the artisan skilled in preparing oral hygiene compositions, including, for example, sucralose, saccharin, cyclamate, acesulfame-K (ACE-K™) and xylitol. Other potential sweetening agents include aspartame and even sucrose, since the presence of CGP in the inventive compositions is likely to obviate the cariogenic potential of the sucrose. Preferably, the sweetening agent is sucralose, and is present in an amount up to about 1%, preferably from about 0.2% to about 0.9% by weight of the total composition.

When present, the flavoring agent is present in an amount effective to impart a pleasant flavor to the composition. The flavoring agent should preferably provide a freshening, cooling, invigorating and/or soothing sensation when the inventive composition is taken into the oral cavity of a mammal. A number of such flavoring agents are known to the artisan skilled in flavoring oral rinse compositions. These include, for example, peppermint, spearmint, wintergreen, menthol, bubble gum, vanilla, orange, lemon, licorice and chocolate flavors, among others, as well as any combination of the above non-mint flavors with a mint flavor. The flavoring agent is present in an amount up to about 35%, preferably from about 20% to about 35% by weight.

In one aspect, the flavoring agent is added to the composition in the form of a concentrate comprising a flavoring composition and a coloring agent. Suitable flavoring compositions and coloring agents and concentrates thereof are well known to the artisan skilled in preparing oral hygiene compositions. Examples of such flavoring concentrates are described herein in the Examples. Preferred concentrates include proprietary Givaudan Roure (Cincinnati, Ohio) flavor concentrates.

Additionally, one or more of certain other inert ingredients may, optionally, be added to formulate the inventive oral rinse compositions. For example, a preservative may be used, such as potassium sorbate; a solubilizer may be used, such as propylene glycol; a smoothing ingredient may be used, such as propylene glycol; a flavor enhancer may be used, such as rhamnose and propylene glycol; and a coloring agent may be used, such as a pale orange coloring agent for orange-mint flavored compositions or blue or green coloring agents for plain mint flavored compositions, among others.

In a preferred embodiment, the ingredients of the inventive oral rinse compositions other than CGP and water do not include ingredients such as alcohol, cetylpyridinium chloride or witch hazel (12–15% ethanol), which should not be ingested by children (See, for example Material Safety Data Sheet, Hazards Identification, for cetylpyridinium chloride). In this embodiment, the compositions of the invention do not require poison control or hazard labeling for children, such as the poison control labeling present on most conventional mouthwashes and mouthrinses. These compositions of the invention do not present the burdens to consumers of protecting themselves and their children against accidental ingestion of the compositions. Moreover, the description by the Foods Chemical Codex (FCC) III listing CGP as a nutrient/dietary supplement means that ingestion by children of these compositions of the invention actually confers a nutritional benefit by providing a source of calcium and phosphorus and/or phosphate. Furthermore, the upper limit of CGP or calcium which can safely be ingested is practically impossible to attain (i.e., greater than 5 grams of CGP per kilogram of body weight in animals) and CGP is described as "generally recognized as safe" by the U.S. Food and Drug Administration (See 21 CFR §182.5201).

Since the inventive compositions are aqueous, the balance of the composition is water. Preferably, the water used is purified to remove all bacteria and objectionable minerals, such as iron and chlorides which impart an unpleasant taste. In a preferred aspect, the water is purified by reverse osmosis. Other purification methods such as filtration and/or distillation may also be used. Procedures for the preparation of several inventive oral rinse compositions are described herein in the Examples.

The invention also includes conveniently portable systems for delivery of a single serving of an oral rinse composition. As used herein, the term "conveniently portable system" means a package or a container which can be conveniently carried on the person, such as in a pocket of a coat or pants or in a pocketbook or pouch to be worn or carried. The conveniently portable system comprises a non-resealable container containing a single serving of an oral rinse composition. The oral rinse composition may be any oral rinse composition, including those conventional oral rinse compositions such as mouthwashes and mouthrinses presently available. Preferably, the oral rinse composition is any one of the oral rinse compositions of the present invention.

In another embodiment, the conveniently portable system is itself a unit of a portable multi-unit package or container containing an oral rinse composition. The portable multi-unit package or container comprises a packaging material which can be any type of packaging material. Preferably, the packaging material is a material such as plastic film, metal foil, paper, and composites thereof. In this embodiment also, the oral rinse composition may be any oral rinse composition, including those conventional oral rinse compositions such as mouthwashes and mouthrinses presently available. Preferably, the oral rinse composition is any one of the oral rinse compositions of the present invention.

Either the single unit or the portable multi-unit package or container may be used by a consumer to deliver a single serving of an oral rinse composition at any time and any place. The consumer can store these compositions, for example, by placing the single unit or the multi-unit package in a car, in a school locker, in a child's lunch box or in a desk at work, or the like. When using the multi-unit package, single units can be removed as desired and opened for delivery of a single serving of the oral rinse composition at virtually any time and place. A single serving can thus be used by the consumer with great convenience without requiring use of a sink or restroom facilities, for example while stopped in a car in traffic, while on an airplane, while in the classroom after a meal or snack at school, or in the office at work before a meeting. Also, one or more single units can be given to guests in hotel room courtesy kits along with soap, shampoo, and other single-use personal products.

In one aspect, the portable system contains a single serving of an oral rinse composition having a volume of from about 5 to about 10 milliliters. In a preferred aspect, the single serving has a volume of about 8 milliliters.

The container may be any container, preferably non-resealable, having a capacity sufficient to contain a single serving of an oral rinse composition, but not so large as to be inconvenient to carry on the person. The container size is preferably about the size of a coffee creamer container, which is normally from about $3/8$ to $5/8$ of an ounce in volume. This size is preferred since volumes greater than about 8 to 10 milliliters of a solution are usually difficult to swish in the mouth without leakage through the lips, even if the mouth is closed. The container dimensions are preferably, for example, about 34 millimeters in diameter by about 24 millimeters in height for cylindrical-shaped containers, and about 1.29 inches in height and 1.34 inches in diameter at the top, and 0.77 inches in diameter at the base for tapered containers. The container is sealed, i.e., it does not contain any aperture, and can be easily opened by a human, even by a child, using only the hands without resort to tools such as can openers, knives or scissors.

The container is preferably non-resealable (i.e., not readily resealable). Thus, once the container is opened and the oral rinse composition is taken therefrom, it is intended that the container and any oral rinse composition remaining therein be discarded. The container is non-resealable because to have the oral rinse composition in a resealable container may encourage people to save the residual oral rinse composition, and this residual material may inadvertently become contaminated and therefore unsuitable for ingestion. Having the oral rinse composition in a nonresealable container encourages people to use an unopened container each time they desire to use a serving of the oral rinse composition. In this way the manufacturer of the article and the public are assured that the manufacturer can exert control over the quality of the contents within the container.

Examples of preferred containers include, for example, a creamer container, a covered cup, a tearable packet, and a blister pack, as well as other packets, containers or packages constructed of a material such as plastic film, metal foil, paper and the like, including composites thereof. The container may be, for example, clear, opaque, fluted or smooth. In one aspect, the container is in the form of a small plastic cup having a peelable cover or lid, much like a jelly, creamer or syrup container made available in some restaurants for delivery of an individual serving to a consumer. When the container is a creamer container or a covered cup, the container has a lid. Preferably, the lid and container are both made of materials which provide a strong vapor barrier such that a minimum amount of evaporation of the product contained therein occurs over a period of months and years. Examples of such materials include impervious plastics, metal foils or foil/paper laminates. Preferably, the container is a creamer container having a metal foil lid.

Several preferred embodiments of the conveniently portable systems of the invention are illustrated in FIGS. 1–4, wherein similar elements are given like reference numerals throughout the drawings. FIGS. 1a and 1b illustrate a preferred embodiment of a single unit 4, in which the container 1 is a creamer container. The lid 2 and the single serving 3 are also indicated in FIG. 1a.

Figure 2B:
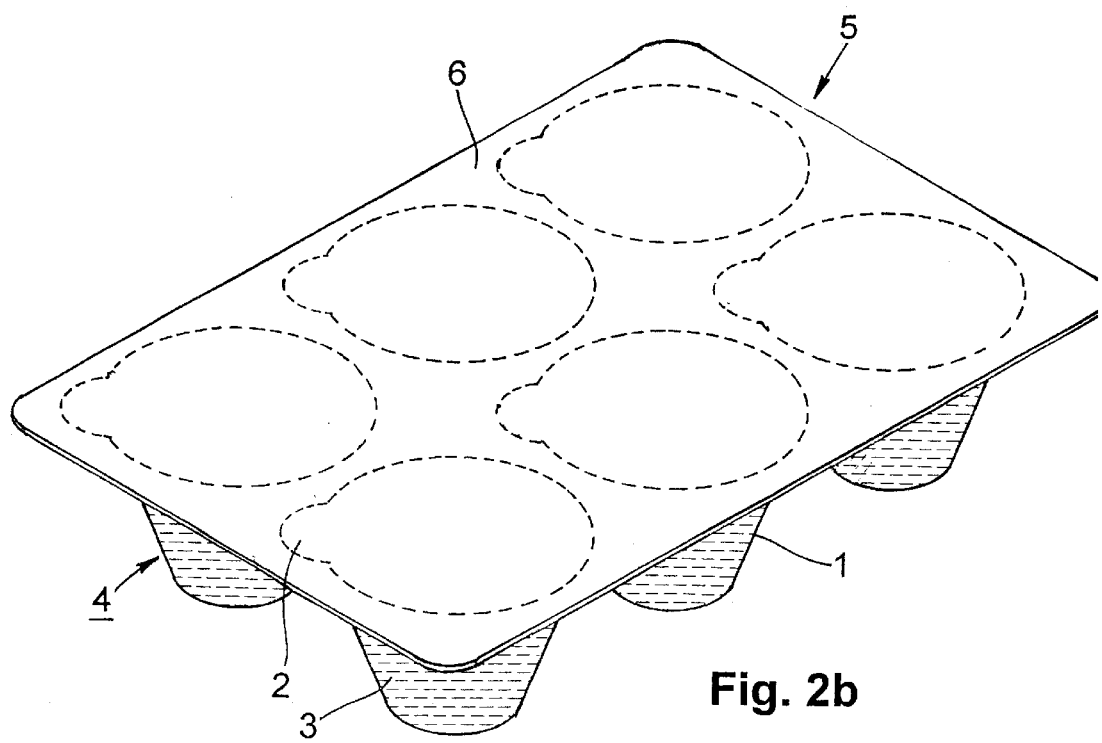
FIGS. 2a and 2b, is a schematic view from the side and perspectively from above, respectively, of a conveniently portable system of the invention in the form of a multi-unit package for delivery of multiple single servings of an oral rinse composition.
Figure 2A:
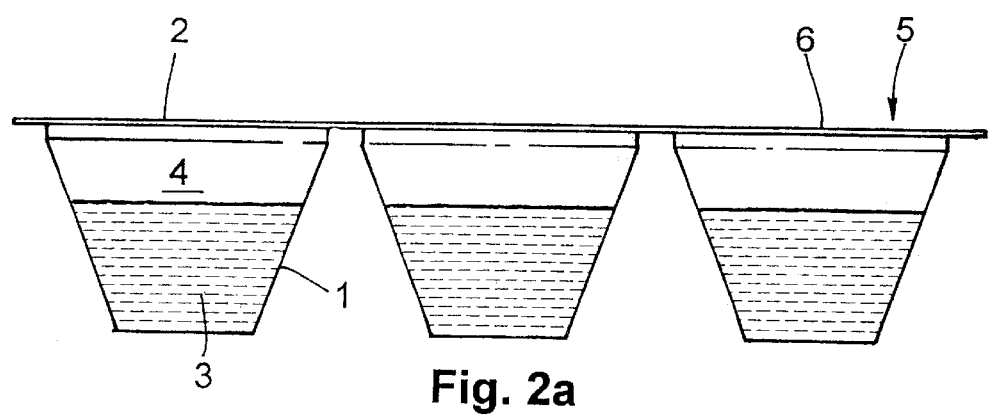

In another preferred embodiment, illustrated in FIGS. 2a and 2b, the conveniently portable system is in the form of a multi-unit package 5 of six single units 4 which comprise creamer containers 1. This multi-unit package can be conveniently carried by the consumer or stored in a locker, a desk, a car, a purse, or the like. The consumer can simply tear out a single unit 4 for use as desired from the multi-unit package 5. The packaging material 6, lids 2 and single servings 3 of the multi-unit package are also indicated in FIGS. 2a and 2b.

In yet another preferred embodiment, illustrated laying on its side in FIG. 3, the conveniently portable system is in the form of an oblong-shaped, portable multi-unit container 5 made of a transparent plastic packaging material 6. This multi-unit container has a "clamshell" type closing cover, which is shown by the arrows in the open (dashed-line) and closed (solid-line) positions. The consumer fills this portable container with several single units 4, as needed, and carries the container in a purse or in a car, for example, for removing single units as desired. When depleted, the multi-unit container is refilled by the consumer with additional single units. The creamer container 1, lid 2 and single serving 3 of a single unit 4 of the multi-unit container are also depicted in FIG. 3.

Figure 4:
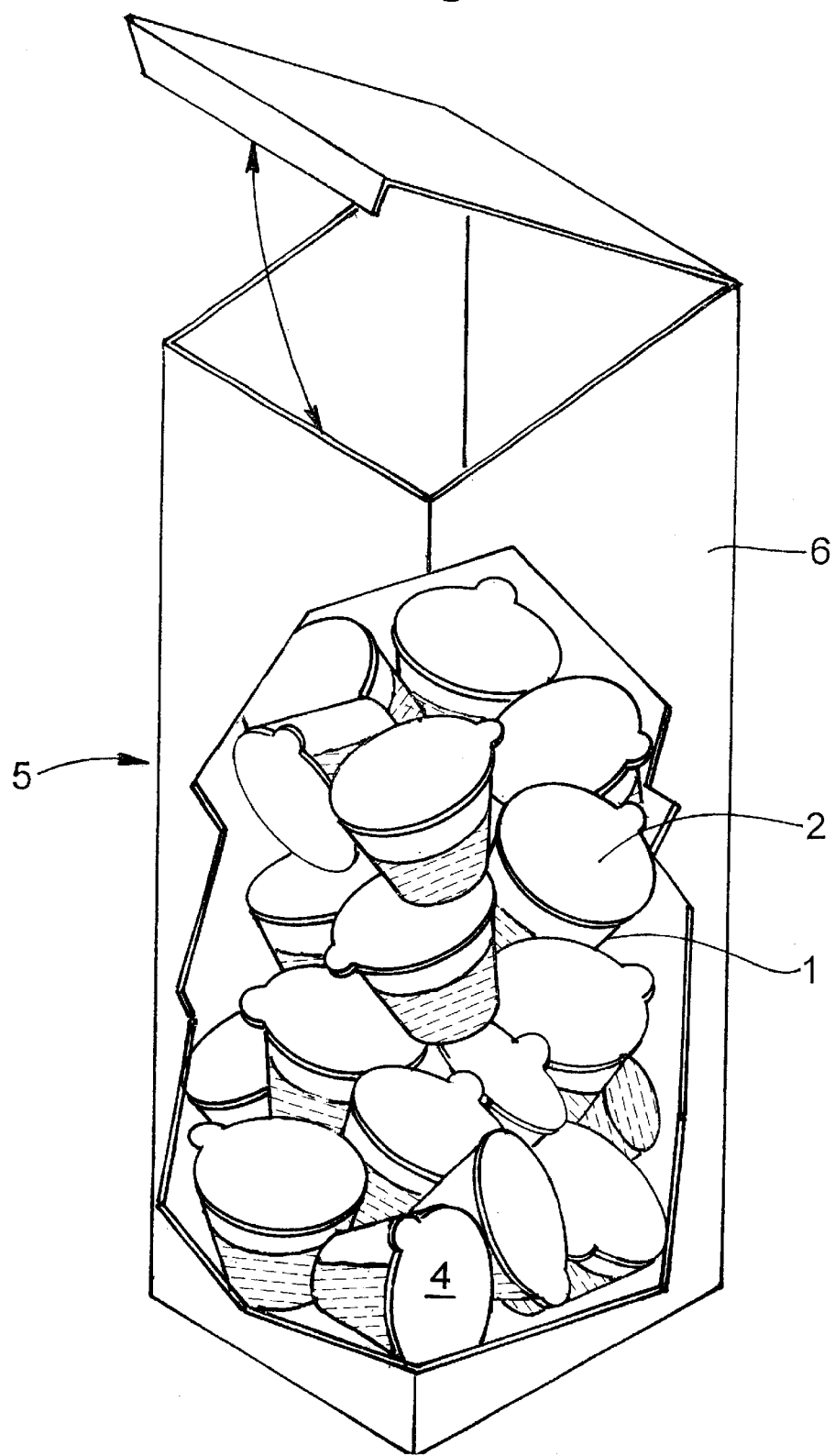
FIG. 4 is a schematic cut-away perspective view from the side of a conveniently portable system of the invention in the form of a "tumble-filled" multi-unit container for delivery of multiple single servings of an oral rinse composition.

In a still further preferred embodiment, illustrated in FIG. 4, the multi-unit container 5 is in the form of a tumble-filled box made of chipboard or paper packaging material 6 and containing, for example, 24 single units 4. The cover of the box may be opened and closed as indicated by the arrows. The box can be used by the consumer in several ways. For example, the box may be used to store many single units 4 at home, in a car, at work, or in a locker for use individually as desired. Alternatively, the box can be used in conjunction with the "clamshell" type multi-unit container described above as a source of single units for refilling the "clamshell" type multi-unit container. The creamer container 1 and lid 2 of a single unit 4 in the multi-unit container are also depicted in FIG. 4.

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Examples 1–3 which follow illustrate several embodiments of the inventive oral rinse compositions which were found to be particularly pleasant in flavor and most effective at freshening and reducing acidity in human subjects during taste and performance testing of the inventive compositions in the methods of the invention. In these Examples, Givaudan Roure (Cincinnati, Ohio) flavoring concentrates were used as flavoring agents and sucralose was used as the sweetening agent. CGP was added to reverse-osmosis purified water in an amount to yield a final concentration of 1% CGP by weight and sucralose was added to yield the various final concentrations indicated. Next, the respective flavoring concentrates were added to yield the various final concentrations indicated. The solutions were then mixed and filtered. After filtration, the solutions were pumped into creamer containers, heat-sealed with metal foil lids, and evaluated in taste and performance tests with human subjects in the methods of the invention. Coloring agents were included in each flavoring concentrate to indicate the flavor type (i.e., pale orange for orange-mint, blue or green for plain mint, etc.).

Example 4 which follows illustrates a procedure for manufacturing several inventive compositions at a manufacturing process scale.

EXAMPLE 1

Preparation of Orange Vanilla Mint Flavored Oral Rinse Compositions

Orange Vanilla Mint flavored oral rinse compositions were prepared as described above using Givaudan Roure (Cincinnati, Ohio) flavoring concentrate #E141570. Three different batches were prepared as described above by diluting the concentrate to a final concentration of 35% by weight in batch 1, 27.6% by weight in batch 2, and 20% by weight in batch 3. Sucralose was added to the solutions of each batch in an amount to yield a final concentration of 0.82% by weight in batch 1, 0.64% by weight in batch 2, and 0.47% by weight in batch 3. CGP was added to the solutions of each batch in an amount to yield a final concentration of 1% by weight.

EXAMPLE 2

Preparation of Bubblegum Mint Flavored Oral Rinse Compositions

Bubblegum Mint flavored oral rinse compositions were prepared as described above using Givaudan Roure (Cincinnati, Ohio) flavoring concentrate #E141654. Three different batches were prepared as described above by diluting the concentrate to a final concentration of 35% by weight in batch 1, 28.75% by weight in batch 2, and 22.5% by weight in batch 3. Sucralose was added to the solutions of each batch in an amount to yield a final concentration of 0.35% by weight in batch 1, 0.29% by weight in batch 2, and 0.23% by weight in batch 3. CGP was added to the solutions of each batch in an amount to yield a final concentration of 1% by weight.

EXAMPLE 3

Preparation of Menthol Mint Flavored Oral Rinse Compositions

Menthol Mint flavored oral rinse compositions were prepared as described above using Givaudan Roure (Cincinnati, Ohio) flavoring concentrate #E141667. Three different batches were prepared as described above by diluting the concentrate to a final concentration of 35% by weight in batch 1, 28.75% by weight in batch 2, and 22.5% by weight in batch 3. Sucralose was added to the solutions of each batch in an amount to yield a final concentration of 0.5% by weight in batch 1, 0.41% by weight in batch 2, and 0.32% by weight in batch 3. CGP was added to the solutions of each batch in an amount to yield a final concentration of 1% by weight.

EXAMPLE 4

Manufacturing Process for the Inventive Oral Rinse Compositions

The following process was used to manufacture 2.5 liters (312×8 milliliter servings) of each of the three inventive oral rinse compositions described below. The water used was purified by reverse-osmosis (Culligan AC-30). A holding tank with a volume of about 3 liters or greater was used. All volume measurements were made using graduated cylinders. Where additional inert ingredients were added (such as potassium sorbate or polyethylene glycol), the amount of water used was reduced accordingly in order to yield a final volume of 2.5 liters.

Ingredients

In the preparation of Orange Vanilla Mint flavored oral rinse compositions, the following ingredients were used:
  a) 875 milliliters of Givaudan-Roure 35% flavoring concentrate #E141570;
  b) 28.75 grams of CGP (for a final concentration of 1.15%);
  c) 16.25 grams of liquid sucralose (for a final concentration of 0.65%), and
  d) 1580 milliliters of purified water.

In the preparation of Bubblegum Mint flavored oral rinse compositions, the following ingredients were used:
  a) 875 milliliters of Givaudan-Roure 35% flavoring concentrate #E141654;
  b) 28.75 grams of CGP (for a final concentration of 1.15%);
  c) 17.5 grams of liquid sucralose (for a final concentration of 0.7%), and
  d) 1578.75 milliliters of purified water.

In the preparation of Menthol Mint flavored oral rinse compositions, the following ingredients were used:
  a) 875 milliliters of Givaudan-Roure 35% flavoring concentrate #E141667;
  b) 28.75 grams of CGP (for a final concentration of 1.15%);
  c) 22.5 grams of liquid sucralose (for a final concentration of 0.9%), and
  d) 1573.75 milliliters of purified water.

Procedure

Freshly purified water at room temperature (21°C.) was added in the amounts listed above for each flavored composition into the holding tank. CGP was then added in the amount shown above, and the mixture was stirred in the holding tank. Next, sucralose was added in the amounts shown above, and the mixture was stirred. Finally, the flavoring concentrate was added and the mixture was stirred. The resulting solution was slightly turbid.

Next, single unit containers were filled. First, Tygon® tubing was connected from the outlet valve of the holding tank to a sterile filtration cartridge. Additional Tygon® tubing was used to connect the exit valve of the sterile filtration cartridge to a pump which was used as the filling machine (National Instrument, piston pump type FUS-30, Filling unit). The mixture was then pumped through the sterile filtration cartridge (0.22 micron cartridge filter, Millipore, Bedford, Mass.) and dispensed into individual single unit containers (Mirrex® 3004 CL35 cups, American Mirrex Corp., New Castle, Del.). Filled containers were then heat-sealed with lid material (Hueck Foils-HPL603-351, Hueck Foils, L. L. C., Wall, N.J.) for 2–5 seconds each using a heat-sealing machine (AkPharma, Inc., Pleasantville, N.J.). Sealed containers were then vacuum tested for leakage.

It will be appreciated by those skilled in the art that changes could be made to the embodiments described above without departing from the broad inventive concept thereof. It is understood, therefore, that this invention is not limited to the particular embodiments disclosed, but is intended to cover modifications within the spirit and scope of the present invention as defined by the appended claims.

We claim:

1. A method of freshening and reducing acidity in both the mouth and the throat of a mammal, said method comprising
  a) taking into the mouth an aqueous solution comprising calcium glycerophosphate (CGP) in an amount effective to reduce said acidity in the mouth and the throat of the mammal;
  b) maintaining said aqueous solution in the mouth for a period of time sufficient to freshen and reduce said acidity in the mouth of the mammal, and
  c) thereafter swallowing said aqueous solution, whereby both the mouth and the throat of the mammal are freshened, and said acidity in both the mouth and the throat of the mammal is reduced.

2. The method of claim 1, wherein said CGP is present in said aqueous solution in an amount from about 0.1% to about 4% by weight.

3. The method of claim 1, wherein the ingredients of said solution other than CGP and water are selected so as to make the solution ingestible even by children.

4. The method of claim 1, wherein said period of time is from about 2 to about 30 seconds.

5. The method of claim 1, wherein said acidity results from ingestion by said mammal of an acidic ingestible or from a condition selected from the group consisting of post-nasal drip, gastroesophageal reflux, acidophilic bacterial metabolism, bacterial fermentation of food particles, and dental plaque.

6. The method of claim 5, wherein said acidic ingestible includes an acidic beverage selected from the group consisting of coffee, beer, lemonade, soft drinks, fruit juice, tomato juice, wine and at least partially dehydrated versions thereof.

7. The method of claim 5, wherein said acidic ingestible includes an acidic food selected from the group consisting of pickles, citrus-flavored water ices and sherbets, salsa, pickled foods, peppered foods, sweet and sour soup, sauerkraut and foods containing tomato sauce.

8. The method of claim 5, wherein said acidic ingestible includes an acidic medicament selected from the group consisting of aspirin, other non-steroidal anti-inflammatory drugs and vitamin C (ascorbic acid).

9. The method of claim 8, wherein said acidic medicament comprises a particle selectively dissolved in the mouth of the mammal.

10. A swallowable oral rinse composition for freshening and reducing acidity in both the mouth and the throat of a mammal, said composition comprising an aqueous solution of CGP in an amount effective to freshen and reduce acidity in both the mouth and the throat of the mammal, and at least one of a sweetening agent in an amount effective to render said composition palatable and a flavoring agent in an amount effective to impart a pleasant flavor to said composition.

11. The composition of claim 10, wherein said CGP is present in an amount from about 0.1% to about 4% by weight; said sweetening agent is present in an amount from about 0.2% to about 0.9% by weight, and said flavoring agent is present in an amount from about 20% to about 35% by weight.

12. The composition of claim 10, wherein the ingredients other than CGP and water are selected so as to make the composition ingestible even by children.

13. The composition of claim 10, wherein said CGP is present in an amount from about 1% to about 3% by weight.

14. The composition of claim 10, wherein said CGP is present in an amount from about 1% to about 1.15% by weight.

15. The composition of claim 10, wherein said water is purified by a method selected from the group consisting of reverse-osmosis, filtration and distillation.

16. The composition of claim 10, wherein said sweetening agent is selected from the group consisting of sucralose, saccharin, acesulfame-K and xylitol.

17. A conveniently portable system for delivery of a single serving of an oral rinse composition, wherein said oral rinse composition is a swallowable aqueous oral rinse composition comprising CGP in an amount from about 0.1% to about 4% by weight; a sweetening agent in an amount from about 0.2% to about 0.9% by weight, and a flavoring agent in an amount from about 20% to about 35% by weight, said portable system comprising a) a non-resealable container having a capacity sufficient to contain a single-serving of said oral rinse composition, wherein said container can be opened by an adult or a child without the use of any tools and can be conveniently carried on the person in a pocket, and b) a single serving of said oral rinse composition within said non-resealable container.

18. The portable system of claim 17, wherein said portable system is a unit of a portable, multi-unit package or container containing said oral rinse composition.

19. The portable system of claim 17, wherein said single serving has a volume of from about 5 to about 10 milliliters.

20. The portable system of claim 17, wherein said non-resealable container is selected from the group consisting of a creamer container, a covered cup, a tearable packet and a blister-pack.

21. The portable system of claim 17, wherein said non-resealable container comprises a lid made of a material selected from the group consisting of plastic film, metal foil, paper, and a composite thereof.

22. The portable system of claim 17, wherein said container is a creamer container comprising a metal foil lid.

* * * * *